United States Patent [19] [11] Patent Number: 4,505,804
Mase et al. [45] Date of Patent: * Mar. 19, 1985

[54] OXYGEN CONCENTRATION DETECTOR

[75] Inventors: Syunzo Mase, Ama; Shigeo Soejima, Nagoya, both of Japan

[73] Assignee: NGK Insulators, Ltd., Japan

[*] Notice: The portion of the term of this patent subsequent to Oct. 4, 2000 has been disclaimed.

[21] Appl. No.: 383,222

[22] Filed: May 28, 1982

[30] Foreign Application Priority Data

Jun. 4, 1981 [DE] Fed. Rep. of Germany ............ 84969

[51] Int. Cl.³ ............................................. G01N 27/46
[52] U.S. Cl. .................................... 204/425; 204/412; 204/426; 204/427; 204/429; 219/553
[58] Field of Search ........................... 204/15, 421-429; 422/98; 219/505, 553

[56]  References Cited

U.S. PATENT DOCUMENTS

| | | | |
|---|---|---|---|
| 3,924,098 | 12/1975 | Dunn | 219/553 |
| 4,101,454 | 7/1978 | Kulwicki et al. | 219/553 |
| 4,145,272 | 3/1979 | Nakamura . | |
| 4,224,113 | 9/1980 | Kimura et al. | 204/425 |
| 4,265,724 | 5/1981 | Haecker . | |
| 4,293,838 | 10/1981 | Wahlers et al. | 219/553 |
| 4,298,573 | 11/1981 | Fujishiro | 204/426 |
| 4,321,577 | 3/1982 | Carlson | 422/98 |
| 4,407,704 | 10/1983 | Mase et al. | 204/425 |

FOREIGN PATENT DOCUMENTS

| | | | |
|---|---|---|---|
| 30164 | 6/1981 | European Pat. Off. | 204/427 |
| 79246 | 6/1981 | Japan | 204/428 |

Primary Examiner—T. Tung
Attorney, Agent, or Firm—Parkhurst & Oliff

[57] ABSTRACT

The disclosed oxygen concentration detector includes a plurality of resistive bodies at least one of which forms an oxygen concentration cell, and an alternating current of a specific frequency is applied to a selected resistive body so as to raise the temperature thereof, said selected resistive body being adapted to heat the oxygen concentration cell.

10 Claims, 22 Drawing Figures

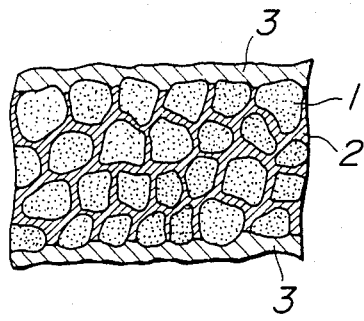
FIG_1
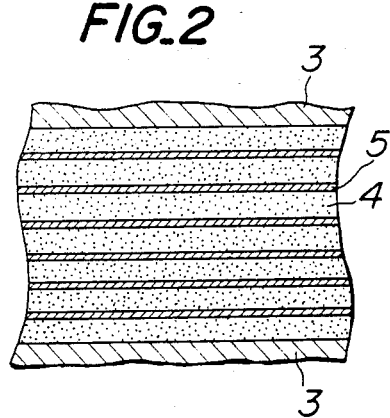
FIG_2
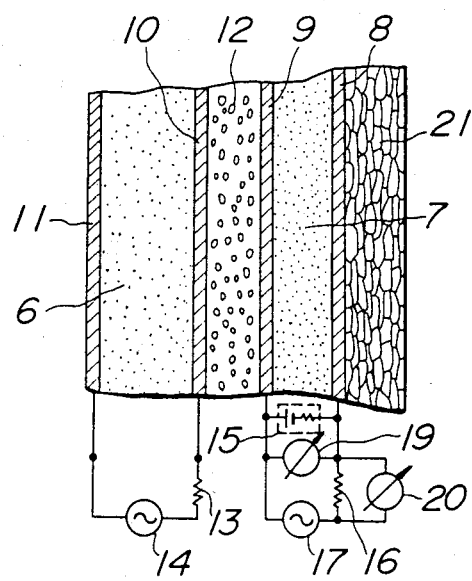
FIG_3

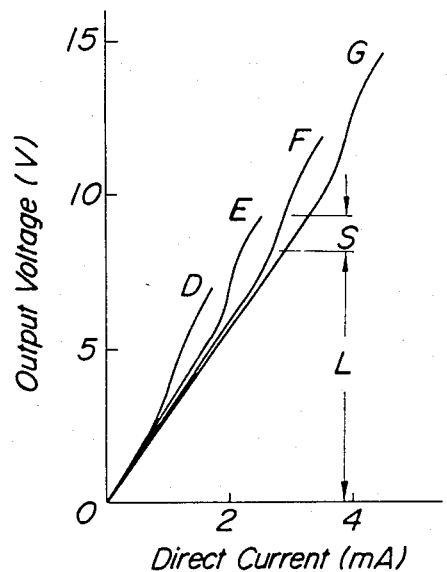
FIG_4
PRIOR ART
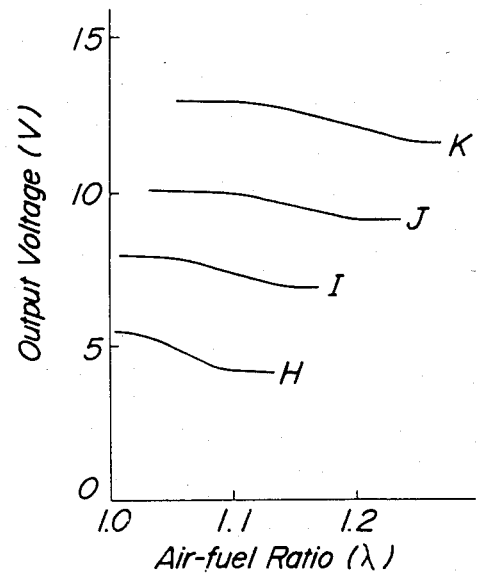
FIG.5
PRIOR ART
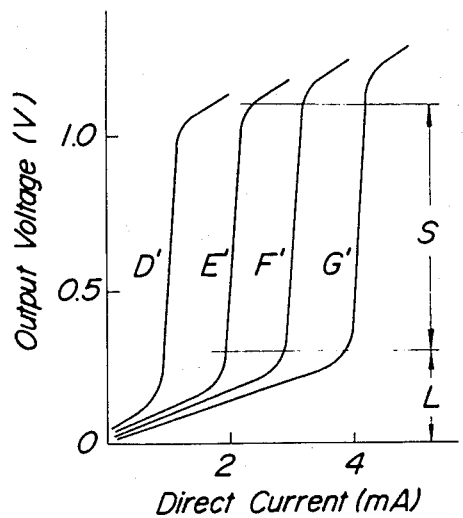
FIG_6
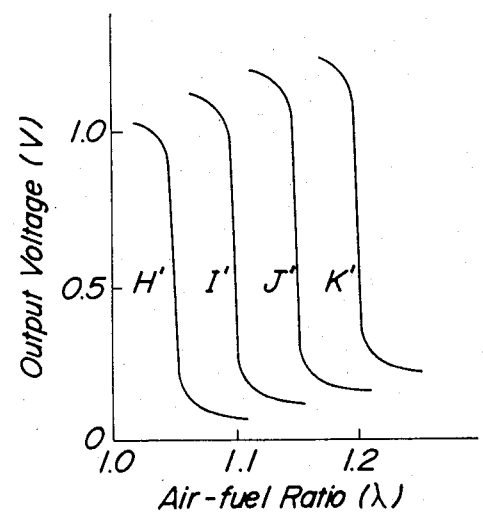
FIG_7

FIG_8
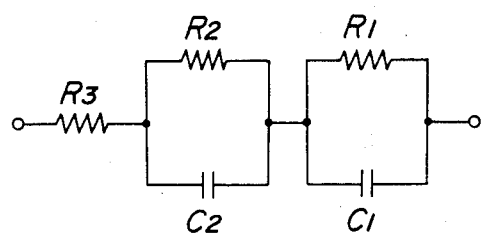
FIG_9
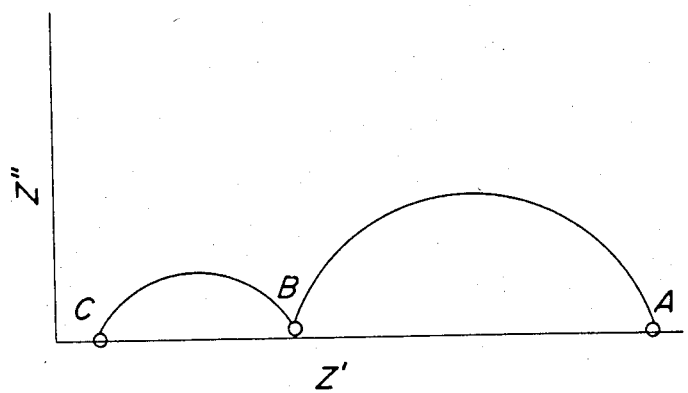

FIG_10
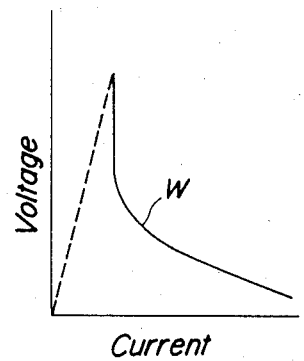
FIG_11
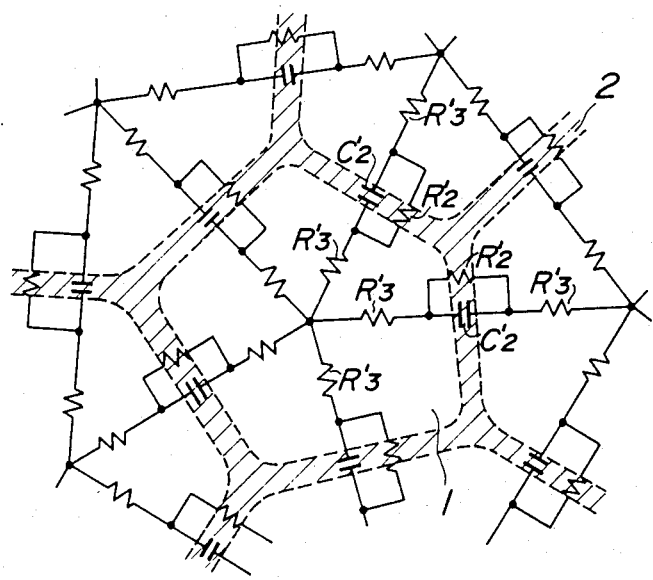

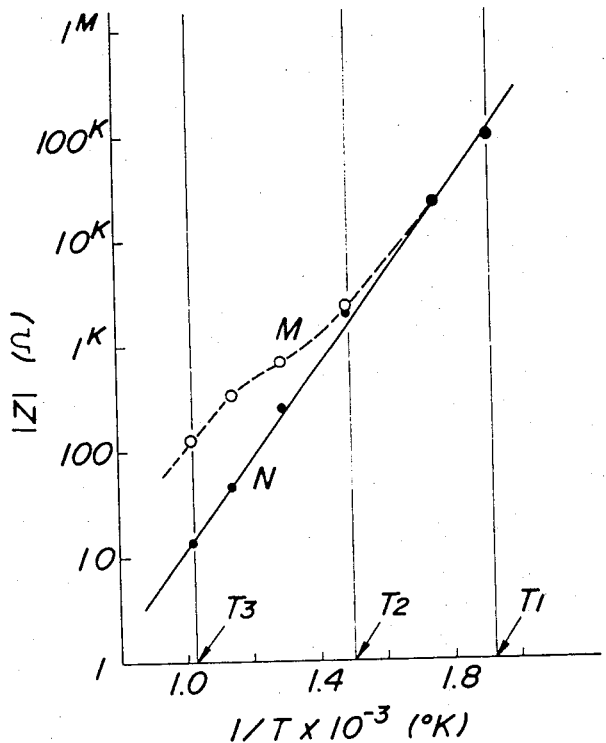
FIG_12
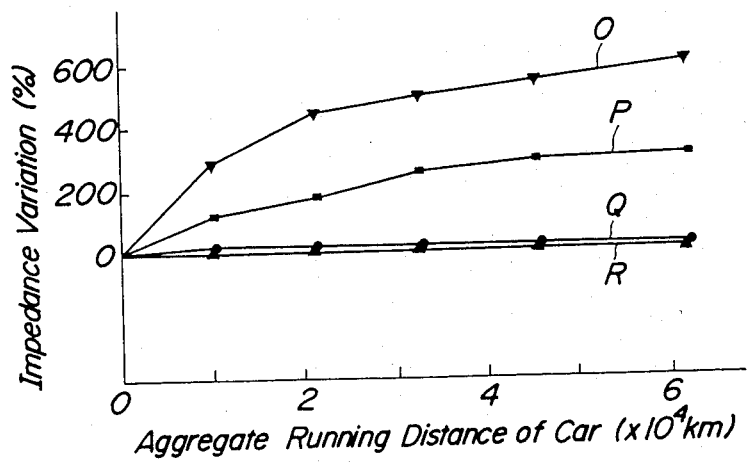
FIG_13

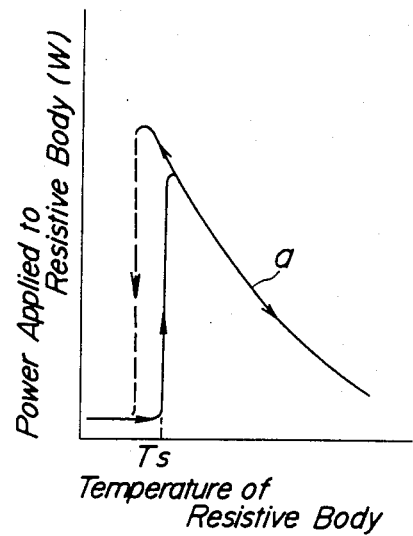
FIG_14
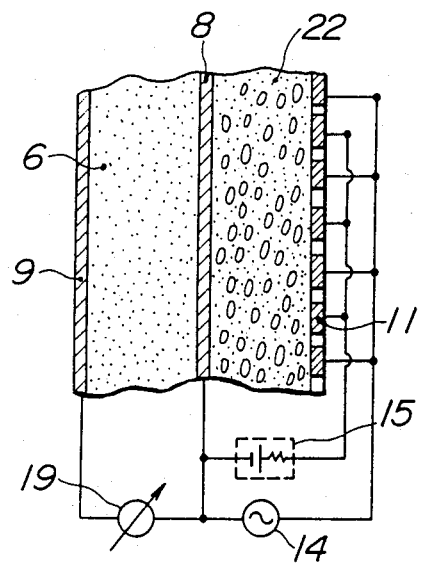
FIG_15
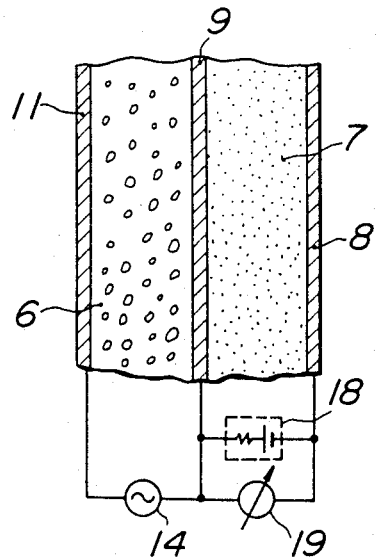
FIG_16

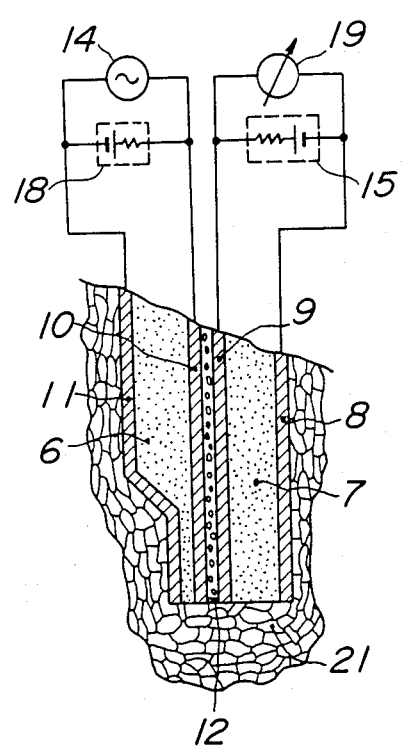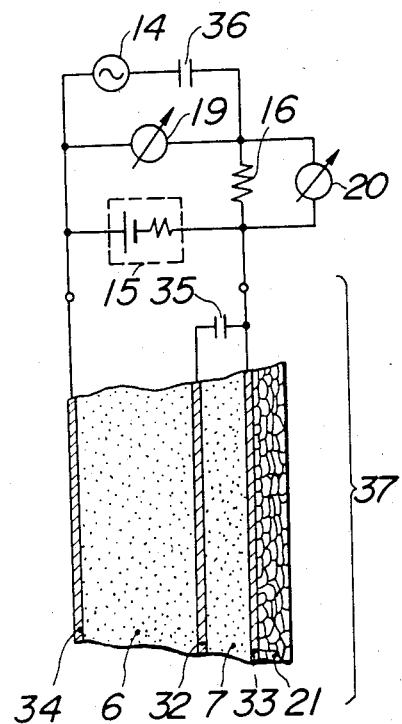

OXYGEN CONCENTRATION DETECTOR

BACKGROUND OF THE INVENTION

1. Field of the Invention

This invention relates to an oxygen concentration detector for detecting the oxygen concentration of a gas, which detector is particularly suitable for detecting the oxygen concentration of a gas at a low temperature.

2. Description of the Prior Art

To measure the oxygen concentration in exhaust gas from internal combustion engines, oxygen concentration detectors made of oxygen-ion-conductive solid electrolyte and based on the principle of an oxygen concentration cell have been used. A typical example of such oxygen concentration detectors uses yttria-added zirconia porcelain as the solid electrolyte with platinum electrodes mounted thereon.

The oxygen concentration detectors of the prior art have shortcomings in that when the temperature of the oxygen concentration detector is low, the catalytic ability of platinum is reduced while the electric resistance of the solid electrolyte is increased and the impedance of the oxygen concentration detector becomes high, and the reduced catalytic ability and the high impedance tend to render the oxygen concentration detector susceptible to adverse effects of noises or the like and to reduce the response speed thereof, and the lowest temperature limit for practical use of the oxygen concentration detector has been about 350° C. On the other hand, the temperature of the exhaust gas from internal combustion engines can be below the above-mentioned lowest temperature limit at the start or during slow running of the engines, so that the conventional oxygen concentration detectors have not been used to their full capability.

To solve this problem, it has been proposed, for instance, to insert a coiled heater wire in a cylindrical solid electrolyte with a bottom, so as to heat the solid electrolyte by the heater wire. However, the use of the heater wire has shortcomings in that the structure becomes complicated, that a large power of up to several tens of watts is necessary, and that the heater wire becomes thin as being used over a long period of time and sometimes the heater wire is broken. The oxygen concentration detectors of the prior art are used to detect the condition that the value of the air-fuel ratio $\lambda$ of an internal combustion engine is 1.0. In order to measure a specific value of the air-fuel ratio $\lambda$ which is different from 1.0, it is not sufficient to accurately measure the electromotive force of an oxygen concentration cell, but the temperature thereof must be measured accurately. To this end, for instance, it has been proposed to dispose a temperature sensing element in a cylindrical solid electrolyte with a bottom for measuring the temperature of the solid electrolyte. However, the use of such temperature sensing element has shortcomings in that the temperature of the solid electrolyte exposed to the exahust gas from an internal combustion engine is not uniform and the temperature measurement at one point thereof does not provide accurate picture of the solid electrolyte temperature; that when the temperature of the exhaust gas is changed the output of the temperature sensing element has a time lag in detecting the temperature change of the solid electrolyte so that the temperature of the solid electrolyte cannot be measured accurately; that the structure of the oxygen concentration detector is complicated.

If the coiled heater wire and the temperature detecting element are inserted in the solid electrolyte for effecting both the heating and the temperature detecting, the structure of the oxygen concentration detector becomes further complicated and unpracticable.

SUMMARY OF THE INVENTION

Therefore, an object of the present invention is to obviate the above-mentioned shortcomings of the prior art by providing an improved oxygen concentration detector which has quick response at low temperatures. The oxygen concentration detector of the invention has a long service life and consumes only a small amount of electric power.

To fulfil the above-mentioned object, the oxygen concentration detector of the invention comprises a plurality of resistive bodies, each of said resistive bodies having a composition including a number of portions with a negative temperature coefficient of electric resistance and high-resistance substance layers separating said portions one from the other, and electrodes mounted on said composition, the impedance of each of said resistive bodies depending only on distributed constants of said composition for frequencies higher than a certain boundary frequency; at least one oxygen-ion-conductive solid electrolyte forming an oxygen concentration cell, said solid electrolyte being one of said resistive bodies; and an AC power source adapted to apply an alternating current to selected one of said resistive bodies which does not form the oxygen concentration cell, so as to heat the selected resistive body, said alternating current having a frequency higher than said certain boundary frequency, said selected resistive body being so related to said oxygen concentration cell that said oxygen concentration cell is heated by said selected resistive body upon application of said alternating current.

In a preferred embodiment of the present invention, a direct current is applied to said oxygen concentration cell or to an oxygen-ion-conductive solid electrolyte formed of one of said resistive bodies, so as to control the oxygen partial pressure at one of electrodes of the oxygen concentration cell.

In another preferred embodiment, an alternating current with a frequency higher than said certain boundary frequency is applied to selected one of said resistive bodies, so as to detect the impedance of said selected resistive body.

An object of the present invention is to provide an oxygen concentration detector for detecting oxygen concentration in gases, comprising a plurality of resistive bodies, each of said resistive bodies having a composition including a number of portions with a negative temperature coefficient of electric resistance and high-resistance substance layers separating said portions one from the other, and electrodes contacting said composition, at least one of said composition being a solid electrolyte forming oxygen concentration cell, at least one of said resistive bodies not being an oxygen concentration cell, an AC power source adapted to apply an AC current to selected one of said resistive bodies which does not form said oxygen concentration cell, so as to heat the selected resistive body, said AC power source being operable at AC frequencies which are not lower than a frequency whose complex impedance characteristics which when graphed in the manner shown in FIG. 9 hereof correspond to point B of said graphed complex impedance characteristics, said selective resistive body being so related to said oxygen concentration cell that said oxygen concentration cell is heated by said selected resistive body upon application of said AC current, and means for measuring a DC potential difference of the oxygen concentration cell.

Another object of the present invention is to provide an oxygen concentration detector for detecting oxygen concentration in gases, comprising a plurality of resistive bodies, each of said resistive bodies having a composition including a number of portions with a negative temperature coefficient of electric resistance and high-resistance substance layers separating said portions one from the other, and electrodes contacting said composition, at least one of said composition being a solid electrolyte forming oxygen concentration cell, and at least one of said resistive bodies not being an oxygen concentration cell, an AC power source adapted to apply an AC current to selected one of said resistive bodies which does not form the oxygen concentration cell, so as to heat the selected resistive body, said AC power source being operable at AC frequencies which are not lower than a frequency whose complex impedance characteristics which when graphed in the manner shown in FIG. 9 hereof correspond to point B of said graphed complex impedance characteristics, said selected resistive body being so related to said oxygen concentration cell that said oxygen concentration cell is heated by said selected resistive body upon application of said AC current, a DC source adapted to apply a DC current to said oxygen ion conductive solid electrolyte forming the oxygen concentration cell, so as to control oxygen partial pressure around at least one electrodes of said oxygen concentratin cell, and means for measuring a DC potential difference of the oxygen concentration cell.

A further object of the present invention is to provide an oxygen concentration detector for detecting oxygen concentration in gases, comprising a plurality of resistive bodies, each of said resistive bodies having a composition including a number of portions with a negative temperature coefficient of electric resistance and high-resistance substance layers separating said portions one from the other, and electrodes contacting said composition, at least two of said composition being oxygen ion conductive solid electrolyte in which at least one is used as an oxygen concentration cell, an AC power source adapted to apply an AC current to selected one of said resistive bodies which does not form the oxygen concentration cell, so as to heat the selected resistive body, said AC power source being operable at AC frequencies which are not lower than a frequency whose complex impedance characteristics which when graphed in the manner shown in FIG. 9 hereof correspond to point B of said graphed complex impedance characteristics, said selected resistive body being so related to said oxygen concentration cell that said oxygen concentration cell is heated by said selected resistive body upon application of said AC current, a DC source adapted to supply a DC current to the oxygen ion conductive solid electrolyte which is not used as the oxygen concentration cell, so as to control oxygen partial pressure around at least one electrode of said oxygen concentration cell, and means for measuring a DC potential difference of the oxygen concentration cell.

A still further object of the present invention is to provide the detector wherein said portions with a negative temperature coefficient of electric resistance are fine grains.

Another object of the present invention is to provide the detector wherein said portions with a negative temperature coefficient of electric resistance are thin films.

Another object of the present invention is to provide the detector wherein an AC current and an AC voltage between the electrode have a negative relation, in which one increases, the other decreases.

Another object of the present invention is to provide the detector wherein the AC current has a frequency at which an impedance of electrostatic capacitance $C_2$ at the highly resistant region layers interposed between the fine grains or thin film is smaller than a resistance $R_2$ at the highly resistant region layers.

Another object of the present invention is to provide the detector further comprising means for detecting the impedance of selected one of said resistive bodies by applying an AC current thereto, said AC current having a frequency which is not lower than a frequency whose complex impedance characteristics which when graphed in the manner shown in FIG. 9 hereof correspond to point B of said graphed complex impedance characteristics.

Another object of the present invention is to provide the detector further comprising an auxiliary heating means related to one of said resistive body.

Another object of the present invention is to provide the detector wherein one electrode of said oxygen concentration cell is connected to one electrode of said resistive body through a capacitor, said selected resistive body being heated by said AC current.

BRIEF DESCRIPTION OF THE DRAWINGS

For a better understanding of the invention, reference is made to the accompanying drawings, in which:

FIG. 1 and FIG. 2 are fractional schematic sectional views of resistive bodies which are used in the oxygen concentration detector of the invention;

FIG. 3 is a diagrammatic illustration of an embodiment of the oxygen concentration detector according to the present invention;

FIGS. 4 through 7 are graphs showing the variation of the voltage across the output terminals of the oxygen concentration cell when a direct current applied therethrough;

FIG. 8 is an equivalent circuit diagram of the resistive body;

FIG. 9 is a graph showing the impedance characteristics of the resistive body;

FIG. 10 is a graph showing the relationship between the voltage and the current through the resistive body;

FIG. 11 is a diagram showing the relationship between the microscopic structure of the resistive body and the equivalent circuit thereof;

FIG. 12 is a graph showing the relationship between the temperature and the impedance of the resistive body;

FIG. 13 is a graph showing the change of the impedance of the resistive body used in an oxygen concentration detector which is mounted on an automobile and the aggregate running distance of the automobile;

FIG. 14 is an explanatory diagram of the temperature self-control characteristics of the oxygen concentration detector of the invention;

FIGS. 15 through 19' are scehmatic diagrams of different embodiments of the oxygen concentration detector according to the present invention;

Figure 19:
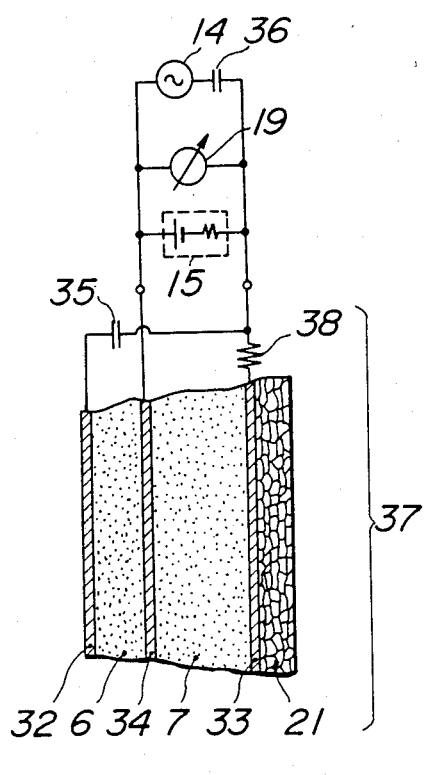

Throughout different views of the drawings, 1 is a fine grain, 2 is a high-resistance substance layer, 3 is an electrode, 4 is a thin film, 5 is a high-resistance substance layer, 6 and 7 are resistive bodies, 8 is a measuring electrode, 9 is a reference electrode, 10 and 11 are electrodes, 12 is a porous substance layer, 13 is a current-limiting resistor, 14 is an AC power source, 15 is a DC power source, 16 is a current-detecting resistor, 17 is an AC power source, 18 is a DC power source, 19 is a DC voltage detector, 20 is an AC voltage detector, 21 is a porous diffusion layer, 22 is a resistive body, 23 is a disk-shaped solid electrolyte, 24 and 25 are electrodes, 26 is a disk-shaped solid electrolyte, 27 and 28 are platinum electrodes 29 is an alumina case, 30 is a porous substance layer, 31 is a diffusion layer, 32 is an electrode, 33 is a measuring electrode, 34 is a reference electrode, 35 is a capacitor, 36 is an AC current-limiting capacitor, 37 is an oxygen concentration detecting unit, and 38 is an AC current-limiting resistor.

DESCRIPTION OF THE PREFERRED EMBODIMENTS

Referring to FIG. 1 showing a practical example of a resistive body to be used in the oxygen concentration detector of the present invention, fine grains 1 have a negative temperature coefficient of electric resistance (to be referred to as NTCR hereinafter) and high-resistance substance layers 2 separate the fine grains 1 from each other. The fine grains 1 and the high-resistance substance layers 2 form a solid electrolyte, and electrodes 3 made of gold or platinum are mounted on opposite end surfaces of the solid electrolyte. For instance, the composition of the resistive body i.e. solid electrolyte is a ceramic material such as ceramics of zirconia ($ZrO_2$) porcelain, $\beta$-alumina ($\beta$-$Al_2O_3$) porcelain, aluminium nitride (AlN), titania ($TiO_2$) porcelain, zinc oxide (ZnO), tin oxide ($SnO_2$), or barium titanate ($BaTiO_3$); or a composition formed by binding fine grains of semiconductor such as metallic silicon (Si) with high-resistance glass or silicon oxide. In such composition, the fine grains 1 are formed of fine crystal grains of $ZrO_2$, $\beta$-$Al_2O_3$, AlN, $TiO_2$, ZnO, $SnO_2$, $BaTiO_3$, or Si, while the high-resistive substance layers 2 are formed of grain boundaries, glass, or silicon oxide. In another embodiment of the present invention as shown in FIG. 1, FIG. 2 shows a different microscopic structure of the resistive body, wherein the thin film 4 is of material having negative temperature coefficient of electric resistance is formed by a suitable method such as sputtering, chemical vapour deposition (CVD), or printing, which thin films 4 correspond to the fine grains 1 of FIG. 1, and high-resistance substance layers 5 are formed so as to separate the above-mentioned films 4 with a negative temperature coefficient of electric resistance one from the other.

FIG. 3 shows a schematic diagram of an embodiment of the oxygen concentration detector according to the present invention. Each of two resistive bodies 6 and 7 comprises a plurality of fine grans with NTCR and high-resistance substance layers separating the fine grains, and the resitive body 6 is an oxygen-ion-conductive solid electrolyte made of titania ($TiO_2$) porcelain, while the other resistive body 7 is an oxygen-ion-conductive solid electrolyte made of zirconia ($ZrO_2$) porcelain. An oxygen concentration cell is formed by mounting a measuring electrode 8 and a reference electrode 9 to the resistive body 7, and the other resistive body 6 is provided with electrodes 10 and 11 and disposed in juxtaposition with the resistive body 7 forming the oxygen concentration cell, while placing a porous substance layer 12 such as an alumina spinel layer therebetween. An AC power source 14 is connected across the electrode 10 of the resistive body 6 on the side of the porous layer 12 and theother electrode 11 thereof, while inserting a current-limiting resistor 13 between the AC power source 14 and the electrode 10 in series. The AC power source 14 has that frequency which causes most of AC polarization to occur in the inside of the resistive body 6. Another AC power source 17 is connected across the measuring electrode 8 and the reference electrode 9 of the resistive body 7 forming the oxygen concentration cell, while serially connecting a current-detecting resistor 16 between the measuring electrode 8 and the AC power source 17. The AC power source 17 also has that frequency which causes most of AC polarization to occur in the inside of the resistive body 7. A DC power source 15 has the positive terminal thereof connected to the reference electrode 9 and the negative terminal thereof connected to the measuring electrode 8, and a DC voltage detector 19 is connected across the DC power source 15. An AC voltage detector 20 is connected across the current-detecting resistor 16, and a porous diffusion layer 21 is provided on the measuring electrode 8. The electrode 11 and the diffusion layer 21 are exposed to a gas to be measured.

In the oxygen concentration detector of the above-mentioned structure, the resistive body 6 connected to the AC power source 14 is adapted to cause self-heating upon application of an alternating current thereto, and the heat generated at the resistive body 6 is transmitted to the resistive body 7 forming the oxygen concentration cell through the porous layer 12. Whereby, the low-temperature performance of the oxygen concentration cell is improved. The heating of the oxygen concentration cell is effected from the resistive body 6 and the heating can be localized to the area where the heating is necessary, so that the power necessary for the heating can be minimized. Furthermore, the oxygen concentration on the measuring electrode 8 can be contolled by applying a direct current to the resistive body 7 from the DC power source 15. More particularly, oxygen in the gas being measured diffuses toward the measuring electrode 8 through the porous diffusion layer 21 at a diffusing speed proportional to the oxygen concentration difference across the opposite ends of the diffusion layer 21. The thus diffusing oxygen ionize at the boundary between the measuring electrode 8 and the resistive body 7 through the following reaction.

$$O_2 + 4e \rightarrow 2O^{--}$$

The oxygen ions then move through the resistive body 7 until arriving at the reference electrode 9 where they are reconverted into oxygen gas and emitted therefrom. Accordingly, there is the following relationship between the oxygen concentration Co in the gas being measured and the oxygen concentration Ce at the boundary between the measuring electrode 8 and the resistive body 7.

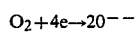

$$Ce = Co - KI/nF.$$

Here, I represents the current density of the direct current flowing through the measuring electrode 8, K is a constant representing the diffusion resistance of the diffusion layer 21 for oxygen gas, n is a charge number in the reaction at the electrode which charge number is 4 in this case, and F is the Faraday constant. As can be seen from the Nernst equation, the electromotive force of an oxygen concentration detector using the principle of the oxygen concentration cell varies suddenly for slight excess oxygen or slight excess fuel in the atmosphere of nearly zero (0) oxygen concentration Ce at the boundary between the measuring electrode 8 and the solid electrolyte 7. It is noted that the oxygen concentration Ce at the above-mentioned boundary can be made zero at an arbitrary value of the oxygen concentration Co in the gas being measured, by selecting such values of the constants K and I which render $KI/nF = Co$. Since the electromotive force of the oxygen concentration cell varies suddenly when the oxygen concentration Ce at the above-mentioned boundary is zero, an arbitrary oxygen concentration in the exhaust gas, which oxygen concentration is different from that at the air-fuel ratio $\lambda = 1.0$, can be now detected accurately and easily by regulating the values of K and I. Besides, excess oxygen conditions can be established in the diffusion layer 21 by applying a direct current to the resistive body 7. Accordingly, the electrode 9 acts as a reference electrode, and the conventionally required exposure of the reference electrode to the ambient atmosphere is eliminated. Whereby, the structure of the oxygen concentration detector is simplified and its size can be reduced.

In the present invention, a direct current is applied to the resistive body 7 which is heated by application of an AC voltage thereto, so that even if the temperature of the exahust gas is low, the polarization in the oxygen concentration cell due to the direct current is very low and such polarization can be neglected as compared with the electromotive force of the oxygen concentration cell. More particularly, FIG. 4 through FIG. 7 show the output voltage of the oxygen concentration cell for the exhaust gas of about 450° C.: namely, FIG. 4 and FIG. 5 give current vs. output voltage curves and air-fuel ratio vs. output voltage curves for a conventional oxygen concentration cell without AC heating, while FIG. 6 and FIG. 7 give current vs. output voltage curves and air-fuel ratio vs. output voltage curves for the oxygen concentration cell which is heated by the AC voltage. The curves D, E, F, and G of FIG. 4 and the curves D', E', F', and G' of FIG. 6 show the relationship between the direct current and the output voltage of the oxygen concentration cell for exhaust gases having oxygen concentrations of 1%, 2%, 3%, and 4%, respectively. The curves H, I, J, and K of FIG. 5 and the curves H', I', J', and K' of FIG. 7 show the relationship between the air-fuel ratio $\lambda$ and the output voltage (V) of the oxygen concentration cell for direct currents of 1 mA, 2 mA, 3 mA, and 4 mA, respectively. The air-fuel ratio $\lambda$ of 1.1 corresponds to an oxygen concentration of about 2% in the exhaust gas, and $\lambda = 1.2$ corresponds to about 4% oxygen concentration. As can be seen from FIG. 4 and FIG. 6, with increase of the direct current, the output voltage of the oxygen concentration cell suddenly increases in a step-like fashion at certain values of the direct current, and the increment of the such step-like increase as represented by the symbol S in FIG. 4 and FIG. 6 is about 1 V irrespectively of heated or not. Such increment substantially corresponds to the electromotive force of the oxygen concentration cell. In the case of FIGS. 4 and 6, if the oxygen concentration is 2%, the step-like change of the output voltage occurs at 2 mA of the direct current as shown by the curves E and E'. In the case of the conventional oxygen concentration cell without heating as shown in FIG. 4, the value of the polarization L due to the direct current through the oxygen concentration cell is several volts to over 10 V, which is large as compared with the step-like change S of about 1 V. Besides, the value of the polarization L varies considerably depending on the temperature of the exhaust gas. Accordingly, it has been dfficult to detect the air-fuel ratio $\lambda$ from the output voltage of the oxygen concentration cell including both the large polarization L due to the direct current and the step-like change S. The operating conditions which allow such a large polarization L tend to cause chipping of the electrodes and the chemical change of the solid electrolyte, so that long service life could not be expected. On the other hand, in the case of the heated oxygen concentration detector according to the present invention as shown in FIG. 6, the step-like change S is about 1 V which is substantially the same as that of the prior art, while the polarization L due to the direct current through the oxygen concentration cell is 0.2 to 0.3 V and hardly affected by the temperature of the exhaust gas, and such polarization is negligible as compared with the step-like change S or the electromotive force of the oxygen concentration cell. Besides, in the detector of the invention, the direct current through the oxygen concentration cell does not cause any adverse effects on the electrodes and the solid electrolyte. As regards the output voltage change characteristics for the air-fuel ratio $\lambda$, the oxygen concentration detector of the invention provides step-like change of the output voltage from about 0.3 V to about 1 V as shown in FIG. 7, so that the air-fuel ratio $\lambda$ can be controlled accurately and easily for instance by selecting a reference value at the output voltage of 0.6 V.

In the heating of the resistive body according to the present invention, an AC power source with that frequency which causes the AC polarization to occur mainly in the inside of the resistive body is used. The reason for using such AC frequency will be explained now.

FIG. 8 shows an electrical equivalent circuit of the resistive body having electrodes as shown in FIG. 1 or FIG. 2, which resistive body has a composition including the above-mentioned fine grains or thin films with a NTCR and high-resistance substance layers separating the fine grains or thin films one from the other and electrodes mounted on the composition. In the equivalent circuit of FIG. 8, $R_1$ is a polarization resistance component at the boundary between the electrode and the resistive body, $C_1$ is an electrostatic capacitance component due to the polarization at the boundary between the electrode and the resistive body, $R_2$ is a resistance component at the high-resistance substance layer 7 or 7A between the NTCR fine grains or thin films, $C_2$ is an electrostatic capacitance component of the high-resistance substance layer, and $R_3$ is a resistance component of the NTCR of fine grains or thin films. The frequency characteristics of the complex impedance $Z = Z' - jZ''$ of the resistive body, as represented by the equivalent circuit of FIG. 8, includes two continuous arcuate portions as shown in FIG. 9. In FIG. 9, the resistance value of point A corresponds to the sum of the three resistance components $R_1+R_2+R_3$ of FIG. 8, the resistance value of point B corresponds to the sum of the two resistance components of $R_2+R_3$, and the resistance value of point C corresponds to the resistance component $R_3$. The polarization of the resistive body from the point A to the point B on the frequency characteristics curve of FIG. 9 is mainly due to the resistance component $R_1$ and the capacitance component $C_1$, and that from the point B to the point C is mainly due to the resistance components $R_2$, $R_3$ and the capacitance component $C_2$. As regards the variation of the complex impedance characteristics with the frequency variation, the point A represents DC, and as the frequency increases, the complex impedance characteristics varies along the arcuate locus toward the point B and further along the other arcuate locus toward the point C.

The arcuate characteristics from the point A to the point B of FIG. 9 varies considerably depending on the surface conditions of the resistive body, on the manner in which the electrodes are mounted on the resistive body, and on the time length of using the resistive body. Accordingly, if an AC voltage of a frequency in the range between the points A and B is used, it is difficult to apply electric power necessary for the heating in a stable fashion. When the resistive body is designed for use at a high temperature and electrodes of refractory materials such as platinum electrodes are used, or when solid electrolyte is used as the resistive body, the arcuate locus between the points A and B of FIG. 9 generally becomes very large at lower temperatures. Accordingly, if the frequency in the range between the points A and B is used in such cases, high voltages are generated at the boundaries between the electrodes and the resistive body, and such high voltages tend to cause chipping of the electrodes, chemical decay of the resistive body surface, electric discharges, induction interferences, and other adverse effects.

On the other hand, in the heating of the resistive body according to the present invention, an alternating current of that frequency which generates polarization mainly in the inside of the resistive body, i.e., the frequency higher than that for the point B of FIG. 9, is applied to the resistive body. Thus, even when the AC current is large enough for heating the resistive body, no chipping of the electrodes and no chemical decay and no breakage of the resistive body are caused. The reason for the elimination of the electrode chipping and the electrolyte decay appears to be in that, when an AC voltage with a frequency higher than that for the point B of FIG. 9 is applied to the resistive body, most of the polarization occurs in the composition of the resistive body represented by the components $R_2$, $C_2$, and $R_3$ collectively showing the distributed constants thereof, and the polarization within the resistive body composition is uniformly distributed in the direction of the thickness thereof, whereby chemical change or decay due to electric current therethrough hardly occur. Furthermore, at the boundaries between the electrodes and the resistive body represented by the components $R_1$ and $C_1$ where electrolyte decay normally occurs, polarization hardly occurs at the frequency above that for the point B of FIG. 9, so that such boundaries are protected against the above-mentioned adverse effects even when being heated quickly. The AC voltage is applied at a frequency which is sufficiently high that the impedance between the electrodes to which the AC voltage is applied is largely independent of the interface capacitances between those electrodes and the surface of the selected resistive body.

Moreover, when the frequency is higher than that for the point B, the impedance of the resistive body is determined by the constants of the resistive body composition, so that the locus is hardly affected by external conditions such as the resistive body surface conditions, the manner in which the electrodes are mounted on the resistive body, and the change hereof with elapse of time. Accordingly, when an AC voltage of the frequency higher than that for the point B of FIG. 9 is used, the impedance of the resistive body becomes smaller than the DC resistance of the resistive body, so that stable heating of the solid electrolyte at a comparatively low voltage becomes possible. To prevent localized heating, even if the frequency higher than that for the point B of FIG. 9 is used, it is preferable to select such fequencies which make the reactance due to the capacitance component $C_2$ of FIG. 8 smaller than the resistive component $R_2$.

FIG. 10 shows the relationship between the alternating current through the resistive body and the AC voltage across the resistive body, provided that the frequency of the AC voltage applied across the electrodes of the resistive body is higher than that for the point B of FIG. 9. In FIG. 10, when the AC current is larger than a certain value, negative co-relation appears between the AC current and the AC voltage, namely, the voltage decreases with the increase of the current as shown by the curve w. This phenomenon is due to the temperature adjusting ability of the resistive body which ability is activated when the resistive body is heated by the alternating current as will be explained hereinafter by referring to FIG. 14. The negative co-relation can be advantageously used, because if the frequency and the amplitude of the alternating current for heating the resistive body are selected in the negative co-relation range of the curve w of FIG. 10, the AC voltage across the resistive body is reduced in response to the flow of the alternating current depending on the temperature of the resistive body reached by the self-heating effect thereof.

The resistance components $R_2$ and $R_3$ and the capacitor component $C_2$ in the electrical equivalent circuit of FIG. 8 do not represent concentrated constants but represent distributed constants as illustrated in the enlarged schematic diagram of FIG. 11. More particularly, the constants are substantially uniformly distributed in the resistive body including the fine grains 1 of thin film 4 with the negative temperature coefficient of electric resistance and the high-resistance substance layers 2 or 5, so that even when the temperature of one distributed resistance component $R_3'$ increases due to some reasons and the resistance value thereof is reduced to allow an increase of the current therethrough, the current i' therethrough is limited by the distributed capacitance component $C_2'$ in series to the distributed resistance component $R_3'$ and the voltage V' applied thereto and the frequency f, i.e., at $i'=2\pi fC_2'Vi$. The voltage V' applied across one portion of the high-resistance substance layer and the distributed capacitance component $C_2'$ are both very small, so that local concentration of the electric current is prevented. Accordingly, with the present invention, the entire resistive body can be uniformly heated without any localized heating even if the resistive body is of plate-like shape and the electrodes are mounted on the opposite surfaces of the plate-like resistive body. On the other hand, the localized heating has been experienced by the conventional heating, such as the heating by using a thermistor of negative characteristics which mainly consists of iron oxide.

In the oxygen concentration detector of FIG. 3, the temperature of the oxygen concentration cell 7 is accurately measured by determining the impedance of the solid electrolyte forming the oxygen concentration cell from the current fed from the AC power source 17 to the oxygen concentration cell 7, which current is detected by the AC voltage detector 20 monitoring the voltage across the current-detecting resistor 16. This detection of the impedance will be explained hereinbelow.

The complex impedance characteristics of the resistive body varies with the temperature of the resistive body, and as the temperature increases, the impedance values at the points A, B, and C of FIG. 9 decreases and the frequencies in the proximity of the points B and C increase. FIG. 12 shows the relationship between the temperature of the resistive body and the impedance thereof for fixed frequencies. As can be seen from the figure of FIG. 12, the temperature of the resistive body i.e. the solid electrolyte can be determined by measuring the impedance thereof. The dashed line curve M of FIG. 12 shows the result of measurement taken by applying alternating currents of that frequency which gives the impedance of the point B of FIG. 9 at the temperature $T_2$, while the solid line curve N shows the result of measurement taken by applying alternating currents of that frequency which gives the impedance of the point C of FIG. 9 at the temperature $T_3$.

To measure the impedance, the present invention uses the AC frequency higher than that for the point B of FIG. 9, namely that frequency which causes most of the AC polarization to occur in the inside of the resistive body, as in the case of the AC frequency for heating the resistive body. The reason for using such AC frequency is in that, referring to the dashed line curve M of FIG. 12 using the frequency of the point B of FIG. 9, if the temperature increases from $T_2$ to $T_3$, the impedance varies from the point B of FIG. 9 to the point A thereof, and impedance in the region between the points A and B is considerably affected by the properties of the electrodes themselves and properties of the boundary between the electrodes and the resistive body. Besides, the impedance in this region is very unstable for the purpose of using the resistive body over a long period of time.

On the other hand, when the above-mentioned AC frequency higher than that for the point B of FIG. 9, namely that frequency which causes most of the AC polarization to occur in the inside of the resistive body, is used, the impedance is stable unless changes occur in the crystal structure or the grain boundary of the resistive body and such stability of the impedance is maintained even after a long period of use. It is more preferable to use the AC frequency in the proximity of that for the point C of FIG. 9, namely that AC frequency at which the impedance of the resistive body depends only on the crystal structure of the resistive body. FIG. 13 clearly shows the advantages of such frequency by illustrating the variation $\Delta Z(\%)$ of the impedance of the oxygen concentration detector at 400° C. with the increase of the aggregate running distance of a car carrying the oxygen concentration detector. In FIG. 13, the curve O is for DC or the frequency for the point A of FIG. 9, the curve P is for the frequency for about the middle point of the arcuate locus between the points A and B of FIG. 9, the curve Q is for the frequency for the point B of FIG. 9, and the curve R is for the frequency for the proximity of the point C of FIG. 9. The curves Q and R for that frequency which causes most of the AC polarization to occur in the inside of the resistive body are high stable even after a long period of use, but the curves O and P are very unstable for use over a long period of time.

The determination of the temperature of the resistive body by measuring the impedance thereof has advantages in the elimination of the time lag and the accuracy in the determination of the actual temperature. Such advantages are useful in accurately carrying out the temperature correction of the diffusion speed of oxygen in the diffusion layer and the temperature correction of the electromotive force, so that the accuracy of the oxygen concentration detector can be improved.

When the AC power source 14 is connected to the resistive body 6 with a negative temperature coefficient of electric resistance through the current-limiting resistor 13 as shown in FIG. 3, the current-limiting resistor 13 prevents any overcurrent from flowing into the resistive body 6. Besides, when the temperature is high and heating is not necessary, the power to be applied to the resistive body 6 can be minimized. The curve a of FIG. 14 shows the negative characteristics of the relationship between the temperature of the gas being measured and the power applied to the resistive body 6, and if the negative characteristics portion of the curve a is used, temperature self-control property is rendered to the resistive body 6, so that the width of temperature change of the resistive body 6 can be made narrower than the width of temperature change of the gas being measured. Whereby the temperature correction of the electromotive force of the oxygen concentration cell is made accurate and easy due to the reduced width of the temperature change. Besides, fluctuation of the diffusion speed of oxygen in the porous diffusion layer 21 of FIG. 3 for temperature changes can be minimized, and the temperature correction thereof is made easy even if required. The current-detecting resistor 13 of FIG. 3 can be replaced with a capacitor or a coil. In FIG. 14, the symbol Ts represents the temperature at which the self-heating of the resistive body starts, and the value of the temperature Ts is determined essentially by the resistance value of the resistive body and the voltage of the AC power source.

It should be noted here that the temperature of the oxygen concentration cell can be kept constant by feeding back the voltage across the current-detecting resistor 16 for impedance detection to the circuit of the AC power source 14 so as to control the electric power applied to the resistive body 6 through regulation of the voltage or frequency of the AC power source 14. The detection of the impedance is preferably carried out at the resistive body 7 forming the oxygen concentration cell as shown in FIG. 3, because such detection is direct, but it is also possible to detect at the resistive body 6 of FIG. 3 or at a resistive body separately provided therefor. In determining the impedance of the heat generating resistive body, the current-limiting resistor may be used as the current-detecting resistor. The current-detecting resistor may be replaced with a capacitor or a coil, as in the case the current-limiting resistor. The frequency of the AC power source for the impedance measurement can be the same as or different from the frequency of the AC power source for heating.

The arrangement of the solid electrolyte, the resistive bodies, the porous layer, and the diffusion layers is not limited to that which is illustrated in FIG. 3. In fact, the position, the number, and the magnitude thereof can be selected so as to meet various requirements of specific use. For instance, in the embodiment of FIG. 15, the function of a diffusion layer 21 is provided in a resistive body 22 by making it porous, which resistive body 22 also forms a solid electrolyte, whereby that air-fuel ratio λ at which the electromotive force of the oxygen concentration detector varies suddenly can be controlled by simultaneously applying the heating and the direct current to the resistive body 22 for causing the movement of the oxygen ions therein. As to the methods of securing the electrodes, FIG. 15 shows an arrangement in which electrodes for heating and electrodes for applying a direct current are separated but mounted on one resistive body 22, so as to use the resistive body 22 or a solid electrolyte for two or more purposes.

As shown in the embodiment of FIG. 16, if the resistive body 6 is made porous, the electrode 9 can be used as a reference electrode without using the porous layer 12 of FIG. 3. In this case if the electrode 9 is exposed to the ambient atmosphere, the electrode 9 can be used as a reference electrode using the oxygen partial pressure of the ambient atmosphere without using any DC power source 18. If a diffusion layer is provided on the measuring electrode 8, that air-fuel ratio λ at which the electromotive force of the oxygen concentration detector varies suddenly can be controlled.

The shape of the solid electrolyte or the resistive body to be used in the oxygen concentration detector of the present invention can be plate-like, cylinder-like, cylinder-like with a bottom end, or thin-film-like. The solid electrolyte or resistive body capable of self-heating may be provided with a portion which is thinner than the remaining portions thereof, so that such thin portion may be hottest in the solid electrolyte or the resistive body, and if such thin portion is disposed adjacent to the oxygen concentration cell with which the exhaust gas is easily brought into contact, the sensitivity and the response of the oxygen concentration detector are both improved.

FIG. 17 shows an embodiment which has the tip portion of the resistive body 6 consisting of solid electrolyte made thin, so as to cause local self-heating at the thin portion. Besides, a direct current is applied to the thin portion, so as to control that value of the air-fuel ratio λ at which the electromotive force of the oxygen concentration cell is suddenly changed. In this embodiment, the porosity of the porous layer 21 must be uniform only at the portion next to that part of the electrode 8 of the solid electrolyte 7 which is adjacent to the self-heating thin portion of the resistive body 6, whereby the steep change of the electromotive force is ensured in the oxygen concentration detector.

More particularly, in conventional oxygen concentration detectors, if the thickness of the diffusion layer is uneven, the diffusion speed of oxygen therethrough becomes uneven, so that a difference is produced between the magnitude of the sudden change in the electromotive force at the thick portion and the magnitude of the sudden change in the electromotive force at the thin portion, whereby the steepness of the overall sudden change of the electromotive force is lost. On the ohter hand, if the heating is caused at a certain localized portion, only such localized portion acts as the main oxygen concentration cell, so that it is sufficient to keep the thickness uniformity of the diffusion layer at such localized portion. Preferably, the diffusion layer for the non-heated portion is made thicker than that for the heated localized portion, or that part of the electrode which faces the non-heated portion of the solid electrolyte is coated with an airtight layer. In this case, the diffusion layer can be made of the same material as that of the porous substance layer or the conventional protective layer made of alumina spinel or the like for protecting the outer electrode against the gas being measured. Even if the heated portion is localized, the present invention determines the temperature of the resistive body or the solid electrolyte by detecting the impedance thereof, so that the temperature of the heated portion or the portion acting as an oxygen concentration cell can be accurately measured.

In the embodiment of FIG. 17, both of the resistive bodies 6 and 7 are provided with the direct currents from the DC power sources 15 and 18 connected thereto, so that the porous substance layer 12 can be brought into the excess oxygen conditions in a very short period of time.

If no direct current is applied to the heated resistive body for causing the oxygen movement, such heated resistive body should preferably be made of materials which are not solid electrolyte. The reason why is in that the resistance value of the solid electrolyte is very high at low temperatures, so that its self-heating start temperature Ts as shown in FIG. 14 becomes high. It is preferable to ensure easy start of the self-heating from room temperature by using the resistive body which is not a solid electrolyte. On the other hand, if a direct current is applied to the heated resistive body for causing oxygen movement, it is necessary to use a solid electrolyte as the resistive body, and in this case it is preferable to ensure good temperature rise of the resistive body by embedding an auxiliary heater in the inside of the resistive body or disposing an auxiliary heater in the proximity of the resistive body. Even if the auxiliary heater is provided, once a slight temperature rise is caused in the resistive body by the auxiliary heater, the temperature rise of the resistive body is accelerated by the self-heating, so that it is preferable to interrupt the power supply to the auxiliary heater after the self-heating is started.

Furthermore, in the oxygen concentration detector according to the present invention, it is possible to connect an electrode of the resistive body for heating to one of the electrodes of the oxygen concentration cell through a capacitor. For instance, in the embodiment of FIG. 18, an electrode 32 is inserted between the two resistive bodies 7 and 6 formed of solid electrolytes, and a measuring electrode 33 is mounted on the resistive body 7 while a reference electrode 34 is mounted on the other resistive body 6. A diffusion layer 21 made of spinel or the like is mounted on the measuring electrode 33. The measuring electrode 33 is connected to the electrode 32 through a capacitor 35. Whereby an oxygen concentration detecting unit 37 is formed. The oxygen concentration detector of FIG. 18 includes the following electric circuit connected to the oxygen concentration detecting unit 37: namely, an AC power source 14 connected across the electrodes 33 and 34 through a capacitor 36 and a current-detecting resistor 16, the frequency of the AC power source 14 being such that most of the AC polarization is caused in the inside of the solid electrolyte of the resistive body 6, the capacitor 36 being for stopping the direct current and for limiting the alternating current; a DC voltmeter 19 connected across the electrodes 33 and 34; an AC voltage detector 20 connected across the current detecting resistor 16; and a DC power source 15 connected across the electrodes 33 and 34.

In the oxygen concentration detector of FIG. 18, if the capacitive reactance of the capacitor 35 is made sufficiently low for the frequency of the AC power source 14, the alternating current from the AC power source flows through the resistive body 6 for causing self-heating therein, but does not flow into the other resistive body 7. Thus, the resistive body 7 does not have self-heating caused therein but is heated by the heat transmitted from the resistive body 6. The temperature of the solid electrolyte of the resistive body 6 can be accurately determined by measuring the impedance of the resistive body 6 by using the AC voltage detector 20 monitoring the voltage across the current-detecting resistor 16. When the reference electrode 34 is exposed to the ambient atmosphere while disposing the measuring electrode 33 in a gas to be measured such as an automobile exhaust gas, the solid electrolytes of the resistive bodies 6 and 7 having the reference electrode 34 and the measuring electrodes 33 act as an oxygen concentration cell, and such oxygen concentration cell produces an electromotive force in proportion to the difference in oxygen concentration between the measuring electrode 33 exposed to the exhaust gas and the reference electrode 34 exposed to the ambient atmosphere.

More particularly, oxygen molecules $O_2$ in the air become $O^{2-}$ ions in the boundary between the reference electrode 34 and the solid electrolyte of the resistive body 6 through the reaction of $O_2+4e \rightarrow 2O^{2-}$, and the ions $O^{2-}$ thus formed diffuse toward the electrode 32 through the solid electrolyte of the resistive body 6. At the boundary between the solid electrolyte of the resistive body 6 and the electrode 32, the reaction of $2O^{2-} - 4e \rightarrow O_2$ takes place, and then the reaction of $O_2+4e \rightarrow 2O^{2-}$ takes place at the boundary between the electrode 32 and the electrolyte of the resistive body 7. The ions $O^{2-}$ thus formed diffuse through the electrolyte of the resistive body 7, and become oxygen molecules $O_2$ at the boundary between the electrolyte of the resistive body 7 and the electrode 33 through the reaction of $2O^{2-} - 4e \rightarrow O_2$, which oxygen molecules diffuse through the diffusion layer 21 and emanate into the exhaust gas. If the electrode 32 is made in the form of a mesh which is partially in contact with the resistive bodies 6 and 7, the $O^{2-}$ ions from the reference electrode 34 may directly diffuse toward the measuring electrode 33 without exchange of electrons of the above-mentioned reactions at the electrode 32. Since the measuring electrode 33 and the electrode 32 are connected through the capacitor 35, there is no direct current through the capacitor 35, and the electromotive force of the oxygen concentration cell is not affected by the presence of the electrode 32 at all.

In the embodiment of FIG. 18, the DC power source 15 has the positive potential terminal connected to the reference electrode 34 and the negative potential terminal connected to the measuring electrode 33, so that the value of the air-fuel ratio λ of the exhaust gas at which the electromotive force of the oxygen concentration cell varies quickly is adjusted to a value different from 1.0.

The embodiment of FIG. 18 has an advantage in that the solid electrolyte of the resistive body 7 in direct contact with the measuring electrode 33 does not cause any self-heating, so that the measuring electrode 33 is very hard to peel off. Another advantage of the embodiment of FIG. 18 is in that the oxygen concentration detecting unit 37 is highly reliable and easy to handle because the capacitor 35 can be placed in a case of the oxygen concentration detecting unit 37 while the measuring electrode 33 or the reference electrode 34 can be grounded together with the case, and only one lead wire coming from the case of the oxygen concentration detecting unit 37 is sufficient for connection with the outside circuit.

FIG. 19 shows a schematic diagram of another embodiment of the invention, in which the reference electrode 34 is disposed between the resistive bodies 6 and 7 made of solid electrolytes. An electrode 32 is mounted on that surface of the resistive body 6 which is opposite to the reference electrode 34, and a capacitor 35 in series with an AC current-limiting resistor 38 is connected across the measuring electrode 33 mounted on the resistive body 7 and the thus mounted electrode 32. In this embodiment, self-heating is caused in the solid electrolyte of the resistive body 6 but not in the solid electrolyte of the resistive body 7, provided that the capacitive reactance of the capacitor 35 is sufficiently small, so that the measuring electrode 33 is difficult to peel off. By applying a direct current to the solid electrolyte 6 from the DC power source 15, the electromotive force of the oxygen concentration cell can be varied at an arbitrarily selected value of the air-fuel ratio λ. The AC current-limiting resistor 38 may be replaced with a coil, and if the resistive body 7 is sufficiently thick as compared with the resistive body 6, the AC current-limiting resistor 38 can be dispensed with. It is also possible to provide a circuit for detecting the impedance of the solid electrolyte. The solid electrolyte of the resistive body 6 is not required to be an oxygen-ion-conducting solid electrolyte, and only requirement therefor is to have a negative temperature coefficient of electric resistance. The present invention can be modified as shown in FIG. 19'. The resistive body 6 is connected to the AC power source 14 through the electrodes 9, 11 and used for heating. Reference numerals 7, 7' are resistive bodies consisting of a solid electrolyte, the resistive body 7' is connected to the DC power source 15 through electrodes 8 and 10 and serves as an oxygen pump, while the resistive body 7 is connected to the DC volt detector 17 through electrodes 8 and 9 and serves as an oxygen concentration cell.

The invention will be described in further detail by referring to an example.

EXAMPLE

Figure 20:
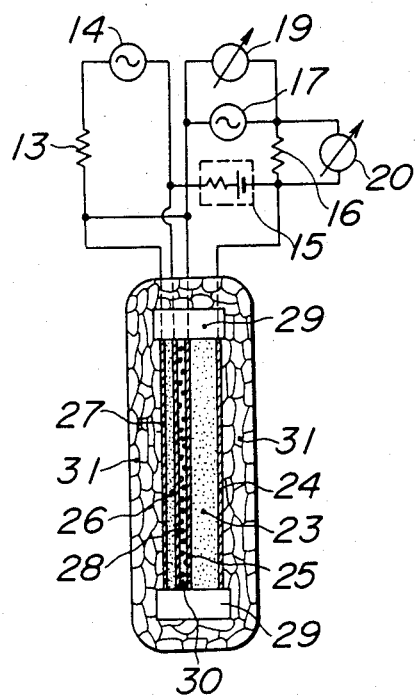
FIG. 20 is an explanatory diagram of an oxygen concentration detector which was tested as an example of the present invention.

Referring to FIG. 20, a disk-shaped solid electrolyte 23 with an outer diameter of 5 mm and a thickness of 1 mm was prepared by using zirconia ($ZrO_2$) porcelain consisting of 100 parts of a mixture of 95 mol% zirconia ($ZrO_2$) and 5 mol% yttria ($Y_2O_3$) and 3 parts of clay. An oxygen concentration cell was formed by mounting platinum electrodes 24 and 25 on opposite surfaces of the solid electrolyte 23. A disk-shaped solid electrolyte 26 with an outer diameter of 5 mm and a thickness of 0.3 mm was prepared by using similar zirconia ($ZrO_2$) porcelain consisting of 100 parts of the mixture of 95 mol% zirconia ($ZrO_2$) and 5 mol% yttria ($Y_2O_3$) and 3 parts of clay, and this solid electrolyte 26 is provided with platinum electrodes 27 and 28 on opposite surfaces thereof. The disk-shaped solid electrolytes 23 and 26 thus provided with electrodes were placed in an alumina (Al$_2$O$_3$) porcelain case 29 while tightly sandwiching a porous substance layer 30 made of alumina spinel therebetween. Lead wires were connected to the electrodes, and a diffusion layer 31 made of alumina spinel was provided on the case 29.

An AC power source 14 with a 30 kHz output voltage of 30 V with sinusoidal waveform was connected across the solid electrolyte 26 through current-limiting resistor 13. A DC power source 15 was connected in series with the solid electrolyte 23 and solid electrolyte 26, so as to cause movement of oxygen from the diffusion layer 31 of the solid electrolytes 23 and 26 to the porous substance layer 30. Another AC power source 17 for impedance detection was connected across the solid electrolyte 23 forming an oxygen concentration cell through a current-detecting resistor 16. A DC voltage detector 19 was connected across the solid electrolyte 23. Whereby an example of the oxygen concentration detector of the invention was produced. The oxygen concentration detectror thus produced was placed in an engine exhaust gas system at about 250° C. with known levels of air-gas ratio λ. The current from the DC power source 15 was set at 2 mA. The response of the output voltage of the oxygen concentration cell was measured by changing the air-fuel ratio λ from 0.9 to 1.1 without direct current and from 1.0 to 1.2 with direct current.

For reference, measurement were also taken without heating. The current-limiting resistor 13 had a resistance of 300Ω. The result of the measurement is shown in Table 1. As can be seen from Table 1, the response speed of the sample of the invention was very good, while in the case of measurement without heating the voltage of the DC power source 15 became more than 120 V and cracks were formed on the solid electrolytes 24 and 26, and the response speed could not be measured.

TABLE 1

| Art | Heating | Direct current | Response speed (mS) |
|---|---|---|---|
| The invention | Heated | Applied | 20 |
| | Heated | Not applied | 20 |
| Reference | Not heated | Applied | Unmeasurable |
| | Not heated | Not applied | 910 |

Note:
The response speed is the time necessary for output voltage change from 0.6 V to 0.3 V without direct current, and from 0.8 V to 0.5 V with direct current.

Figure 21:
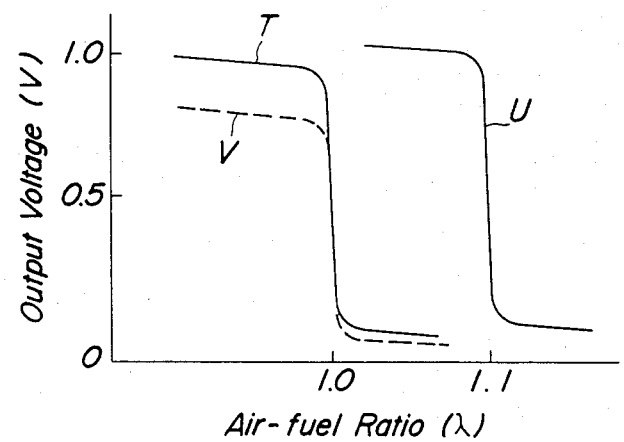
FIGS. 21 and 22 are graphs showing the results of tests which were conducted on the example of FIG. 20.

The output voltage of the oxygen concentration cell was measured at the exhaust gas temperature of 250° C. while changing the air-fuel ratio λ but maintaining other conditions of the engine exhaust gas system constant, for both with the direct current of 2 mA from the DC power source 15 and without the direct current. For reference, similar measurements were taken on the prior art without heating. The result is shown in FIG. 21, wherein the curves T and U are for the case of the present invention with heating by the AC current and the curve V is for the prior art. The curves T and V are for the case without the direct current and the curve U is for the case with the direct current. As can be seen from FIG. 21, the change of the electromotive force was steep even in the case of the curve U of the invention with the application of the direct current. On the other hand, when the direct current was applied without heating (not shown), the output voltage increased in excess of 120 V and steep change of the output voltage was not detected.

The temperature of the solid electrolyte 23 was determined by measuring the impedance of the solid electrolyte 23 forming the oxygen concentration cell by changing the temperature of the exhaust gas in three steps i.e., 250° C., 450° C., and 650° C., while using the samples of the same engine exhaust gas system and keeping the air-fuel ratio λ at 0.9 without direct current. At the same time, the power applied to the solid electrolyte 26 and the electromotive force of the oxygen concentration cell were measured. For reference, measurement was taken on a conventional oxygen concentration detector having a temperature detecting element disposed in a cylindrical solid electrolyte with a bottom. The result is shown in Table 2.

As shown in Table 2, the temperature of solid electrolyte as determined by the impedance was in good agreement with the temperature thereof directly measured. For the variations of the exhaust gas temperature, the temperature change of the solid electrolyte was about one third.

Thereafter, the engine rotating speed was suddenly raised from 1,000 rpm to 4,000 rpm while keeping the air-fuel ratio λ of the engine exhaust gas system at 1.1, and the temperature change of the exhaust gas was measured, and simultaneously the temperature change of the solid electrolyte was determined by measuring the impedance variation. For reference, measurement was taken on a conventional oxygen concentration detector having a temperature detecting element disposed in a cylindrical solid electrolyte with a bottom.

Figure 22:
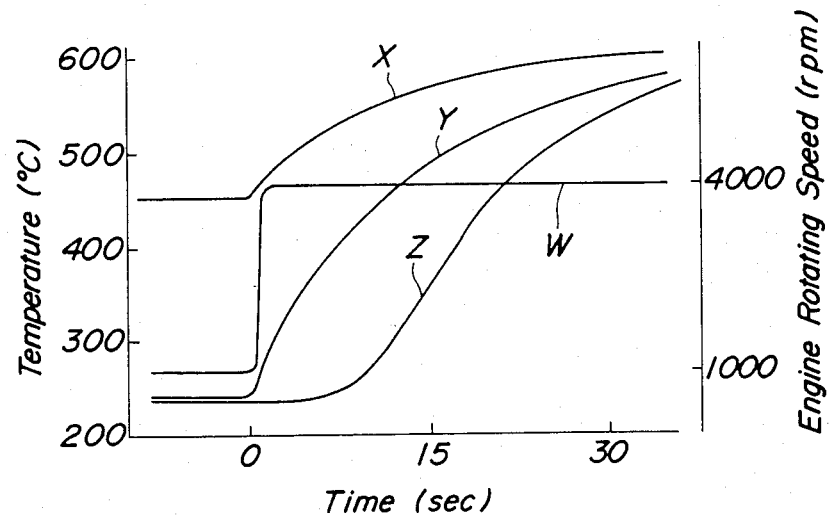

The result of the measurements is shown in FIG. 22, wherein the curve W shows the variation of the rotating speed, the curve X shows the temperature variation of the solid electrolyte measured by the impedance according to the present invention, the curve Y shows the variation of the exhaust gas temperature, and the curve Z shows the temperature change of the solid electrolyte as determined by the conventional temperature detecting element.

| Exhaust gas temperature (°C.) | Art | Impedance of solid electrolyte (Ω) | Temperature determined by impedance (°C.) | Temperature of solid electrolyte directly measured (°C.) | Power applied to solid electrolyte (W) | Output voltage (V) |
|---|---|---|---|---|---|---|
| 250 | The | 36 | 520 | 522 | 3.9 | 0.90 |
| 450 | invention | 12 | 560 | 558 | 1.7 | 0.90 |
| 650 | | 2.5 | 660 | 665 | 0.3 | 0.89 |
| 250 | Prior art | | | 240 | | 0.73 |
| 450 | | | | 438 | | 0.90 |
| 650 | | | | 635 | | 0.89 |

As can be seen from FIG. 22 when the engine rotating speed suddenly changed, the temperature of the exhaust gas increased along the curve Y and the temperature of the solid electrolyte also increased, and curve X showing the temperature change of the solid electrolyte measured by the impedance according to the present invention did not have any substantial time lag relative to the exhaust gas temperature change of the curve Y. On the other hand, the curve Z showing the temperature change of the solid electrolyte measured by the conventional temperature detecting element had a considerably large time lag relative to the curve Y showing the temperature change of the exhaust gas, so that the measurement by the conventional temperature detecting element was apparently inaccurate for the purpose of temperature correction of the electromotive force of the solid electrolyte and the temperature correction of the diffusion speed of the diffusion layer in response to the variation of the exhaust gas.

As described in the foregoing, in the oxygen concentration detector according to the present invention, the solid electrolyte is self-heated in a stable fashion over a long period of time by applying a comparatively low AC voltage thereto, so that oxygen concentration of exhaust gas can be detected with a quick response even if the temperature of the exhaust gas is low. Even when the output voltage of the oxygen concentration cell is low, deposition of carbon or the like on the porous solid electrolyte or the diffusion layer is minimized. That value of the air-fuel ratio $\lambda$ at which the electromotive force of the oxygen concentration cell varies suddenly can be accurately controlled to the lean burn zone or to the rich burn zone by applying a direct current, without requiring exposure of the reference electrode to the ambient atmosphere. Besides, the temperature of the solid electrolyte can be accurately measured without any time lag over a long period of use. In the present invention, local heating of the solid electrolyte can be easily carried out, so as to minimize the electric power for the heating, and the steep sudden change of the electromotive force can be achieved by keeping the uniform thickness of the diffusion layer only at the portion corresponding to the localized heated portion. The self-heating of the solid electrolyte can provide the temperature self-control function, so that even when the temperature of the porous solid electrolyte or the diffusion layer is changed, the change in the diffusion speed is kept small, whereby fluctuation in that air-fuel ratio $\lambda$ at which the electromotive force changes suddenly due to the change in the diffusion speed is minimized. Thus, the oxygen concentration detector of the present invention has excellent performance in terms of the accuracy, the response, and the durability. As compared with the prior art, the oxygen concentration detector of the invention does not use any separate temperature detecting element and any heater wire, so that the risk of fault due to the breakage of the heater wire is completely eliminated. Furthermore, the structure of the oxygen concentration detector of the present invention is very simple. In summery, the present invention provides an oxygen concentration detector which has the above-mentioned advantages and which is particularly suitable for detection of the oxygen concentration in the exhaust gas from internal combustion engines, so that the invention contributes greatly to the industry.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. An oxygen concentration detector for detecting oxygen concentration in gases, comprising:
    a plurality of resistive bodies, each of said resistive bodies having a composition including a number of portions with a negative temperature coefficient of electric resistance and high-resistance substance layers separating said portions one from the other, and at least two separate electrodes contacting each of said plurality of resistive bodies, each of said resistive bodies being located between said at least two separate electrodes, at least one of said plurality of resistive bodies forming an oxygen concentration cell, at least one other of said plurality of resistive bodies not being an oxygen concentration cell;
    an AC power source connected to said at least two separate electrodes contacting said at least one other resistive body, said AC power source applying an AC current to at least one of said other resistive bodies, so as to heat said at least one oother resistive body, said AC power source being arranged to supply an AC voltage at a frequency sufficiently high that an impedance between said at least two electrodes to which AC voltage is appled is largely independent of interface capacitances between said electrodes to which AC voltage is applied and a surface of said at least one other resistive body, said at least one other resistive body being so related to said oxygen concentration cell that said oxygen concentration cell is heated by said at least one other resistive body upon application of said AC current to said at least two electrodes contacting said at least one other resistive body; and
    means for measuring a DC potential difference of the oxygen concentration cell.

2. An oxygen concentration detector for detecting oxygen concentration in gases, comprising:
    a plurality of resistive bodies, each of said resistive bodies having a composition including a number of portions with a negative temperature coefficient of electric resistance and high-resistance substance layers separating said portions one from the other, and at least two separate electrodes contacting each of said plurality of resistive bodies, each of said resistive bodies being located between said at least two separate electrodes, at least one of said plurality of resistive bodies being a solid electrolyte, thereby forming an oxygen concentration cell, at least one other of said plurality of resistive bodies not being an oxygen concentration cell;
    an AC power source connected to said at least two separate electrodes contacting said at least one other resistive body, said AC power source applying an AC current to at least one of said other resistive bodies, so as to heat said at least one other resistive body, said AC power source being arranged to supply an AC voltage at a frequency sufficiently high such that an impedance between said at least two electrodes to which AC voltage is applied is largely independent of interface capacitances between said electrodes to which AC voltage is applied and a surface of said at least one other resistive body, said at least one other resistive body being so related to said oxygen concentration cell that said oxygen concentration cell is heated by said at least one other resistive body upon application of said AC current to said at least two electrodes contacting said at least one other resistive body;

a DC source connected to said separate electrodes contacting said oxygen ion conductive solid electrolyte forming the oxygen concentration cell, said DC source applying a DC current to said electrolyte for controlling oxygen partial pressure around at least one electrode contacting said oxygen concentration cell; and means for measuring a DC potential of said oxygen concentration cell.

3. An oxygen concentration detector for detecting oxygen concentration in gases, comprising:

a plurality of resistive bodies, each of said resistive bodies having a composition including a number of portions with a negative temperature coefficient of electric resistance and high-resistance substance layers separating said portions one from the other, and at least two separate electrodes contacting each of said plurality of resistive bodies, each of said resistive bodies being located between said at least two separate electrodes, at least two of said plurality of resistive bodies being an oxygen ion conductive solid electrolyte, wherein one of said at least two bodies is used as an oxygen concentration cell and the other is not used as a oxygen concentration cell;

an AC power source connected to said at least two separate electrodes contacting said oxygen concentration cell, said AC power source applying an AC current to at least one of said resistive bodies which does not form the oxygen concentration cell, so as to heat said at least one body not forming the oxygen concentration cell, said AC power source being arranged to supply an AC voltage at a frequency sufficiently high such that an impedance between said at least two electrodes to which AC voltage is applied is largely independent of interface capacitances between said electrodes to which AC voltage is applied and a surface of said selected resistive body, said at least one body not forming the oxygen concentration cell being so related to said oxygen concentration cell that said oxygen concentration cell is heated by said at least one body not forming the oxygen concentration cell, upon application of said AC current;

a DC source connected to said separate electrodes contacting the oxygen conductive solid electrolyte which is not used as the oxygen concentration cell, said DC source applying a DC current to said electrodes for controlling oxygen partial pressure around at least one electrode of said oxygen concentration cell; and means for measuring a DC potential difference of the oxygen concentration cell.

4. The detector of claim 1, 2 or 3, wherein said portions of said resistive bodies with a negative temperature coefficient of electric resistance are fine grains.

5. The detector of claim 1, 2 or 3, wherein said portions of said resistive bodies with a negative temperature coefficient of electric resistance are thin films.

6. The detector of claim 1, 2 or 3, wherein an AC current and an AC voltage applied between the electrodes have a negative relation, such that when one increases, the other decreases.

7. The detector of claim 1, 2 or 3, wherein the AC current has a frequency at which an impedance of electrostatic capacitance at highly resistant region layers interposed between fine grains or thin films is less than a resistance at the highly resistance region layers.

8. The detector of claim 1, 2 or 3, further comprising means for detecting an impedance of one of said at least one resistive bodies by applying an AC current therethrough, said AC current having a frequency sufficiently high such that an impedance between said at least two electrodes to which AC voltage is applied is largely independent of interface capacitances between said electrodes to which AC voltage is applied and a surface of said resistive bodies.

9. The detector of claim 1, 2 or 3, further comprising an auxiliary heating means attached to one of said resistive bodies.

10. The detector of claim 1, 2 or 3, wherein one electrode of said oxygen concentration cell is connected to one electrode of said resistive body through a capacitor, said resistive body being heated by said AC current.

* * * * *